United States Patent
Ghiasi et al.

(10) Patent No.: US 12,070,312 B2
(45) Date of Patent: Aug. 27, 2024

(54) CONTEXTUALLY AWARE FETAL SENSING IN TRANSABDOMINAL FETAL PULSE OXIMETRY

(71) Applicant: The Regents of the University of California, Oakland, CA (US)

(72) Inventors: Soheil Ghiasi, Davis, CA (US); Daniel Fong, Davis, CA (US)

(73) Assignee: The Regents of the University of California, Oakland, CA (US)

(*) Notice: Subject to any disclaimer, the term of this patent is extended or adjusted under 35 U.S.C. 154(b) by 1161 days.

(21) Appl. No.: 16/820,388

(22) Filed: Mar. 16, 2020

(65) Prior Publication Data

US 2020/0214603 A1 Jul. 9, 2020

Related U.S. Application Data (63) Continuation-in-part of application No. 16/347,532, filed as application No. PCT/US2017/062782 on Nov. 21, 2017, now Pat. No. 11,116,412.

(Continued)

(51) Int. Cl.
*A61B 5/1464* (2006.01)
*A61B 5/00* (2006.01)
(Continued)

(52) U.S. Cl.
CPC .......... *A61B 5/1464* (2013.01); *A61B 5/0205* (2013.01); *A61B 5/14552* (2013.01);
(Continued)

(58) Field of Classification Search
CPC . A61B 5/1464; A61B 5/0205; A61B 5/14552; A61B 5/7214; A61B 5/725;
(Continued)

(56) References Cited

U.S. PATENT DOCUMENTS 6,751,498 B1 * 6/2004 Greenberg ............. A61B 5/313
600/511
8,644,900 B2 2/2014 Balberg et al.
(Continued)

FOREIGN PATENT DOCUMENTS

WO 2020010276 A1 1/2020

OTHER PUBLICATIONS

International Search Report and Written Opinion PCT/US2017/062782, Feb. 19, 2018, Korean International Application Division Commisioner.

*Primary Examiner* — Lindsey G Wehrheim
(74) *Attorney, Agent, or Firm* — Park, Vaughan, Fleming & Dowler LLP (57) ABSTRACT

The disclosed system determines a fetal blood oxygenation level. During operation, the system activates two or more light sources, having different wavelengths, which are positioned on the abdomen of a pregnant mammal to direct light into the maternal abdomen toward a fetus. Next, the system receives a set of mixed signals from a set of photodetectors, which are positioned at different locations on the maternal abdomen to receive reflected light that traverses both maternal and fetal tissue. The system then performs a filtering operation that removes signal components associated with a maternal heart rate and a maternal respiration rate from the set of mixed signals to produce a set of fetal signals. Next, the system combines the set of fetal signals to produce a composite fetal signal. Finally, the system determines the fetal blood oxygenation level by performing a pulse-oximetry computation based on the composite fetal signal.

24 Claims, 9 Drawing Sheets

Related U.S. Application Data (60) Provisional application No. 62/424,789, filed on Nov. 21, 2016.

(51) Int. Cl.
  *A61B 5/0205* (2006.01)
  *A61B 5/024* (2006.01)
  *A61B 5/08* (2006.01)
  *A61B 5/1455* (2006.01)

(52) U.S. Cl.
  CPC ............ *A61B 5/7214* (2013.01); *A61B 5/725* (2013.01); *A61B 5/7257* (2013.01); *A61B 5/7278* (2013.01); *A61B 5/02411* (2013.01); *A61B 5/0816* (2013.01); *A61B 5/4356* (2013.01); *A61B 2562/0238* (2013.01)

(58) Field of Classification Search
  CPC . A61B 5/7257; A61B 5/7278; A61B 5/02411; A61B 5/0816; A61B 5/4356; A61B 2562/0238
  See application file for complete search history.

(56) References Cited

U.S. PATENT DOCUMENTS

| | | |
|---|---|---|
| 2004/0116789 A1 | 6/2004 | Boas et al. |
| 2006/0189862 A1 | 8/2006 | Casciani et al. |
| 2006/0241510 A1* | 10/2006 | Halperin .............. A61B 5/7275 600/534 |
| 2009/0281402 A1 | 11/2009 | Chance |
| 2010/0137727 A1 | 6/2010 | Sameni et al. |
| 2011/0218413 A1 | 9/2011 | Wang et al. |
| 2018/0070871 A1* | 3/2018 | Ray ..................... A61B 5/0011 |
| 2018/0256088 A1 | 9/2018 | Ray |

* cited by examiner

| Tissue Type: | $\mu_a$ (mm$^{-1}$) | $\mu_s$ (mm$^{-1}$) | g (unitless) | n (unitless) | z (cm) |
|---|---|---|---|---|---|
| Maternal Abdominal Wall | 0.009 | 12.003 | 0.9 | 1.4 | 0.2 - 4.2 |
| Maternal Uterus | 0.01 | 8.15 | 0.9 | 1.4 | 0.7 |
| Amniotic Fluid | 0.004 | 0.1 | 0.9 | 1.334 | 0.1 |
| Fetal Tissues | 0.013 | 9.916 | 0.9 | 1.4 | 10 |

FIG. 10

CONTEXTUALLY AWARE FETAL SENSING IN TRANSABDOMINAL FETAL PULSE OXIMETRY

CROSS-REFERENCE TO RELATED APPLICATION

This application is a continuation-in-part of, and hereby claims priority under 35 U.S.C. § 120 to, pending U.S. patent application Ser. No. 16/347,532, entitled "Robust, Clinical Grade Transabdominal Fetal Pulse Oximetry," by inventors Soheil Ghiasi and Daniel Fong, filed on 3 May 2019. U.S. patent application Ser. No. 16/347,532, itself claims priority under 35 U.S.C. § 119(b) to Patent Cooperation Treaty Application No. PCT/US2017/062782, entitled "Robust, Clinical-Grade Transabdominal Fetal Pulse Oximetry," by inventors Soheil Ghiasi and Daniel Fong, filed on 21 Nov. 2017. PCT Application No. PCT/US2017/062782 itself claims the benefit of U.S. Provisional Patent Application No. 62/424,789, entitled "Method and Apparatus for Robust-Clinical-Grade Transabdominal Fetal Blood Oximetry," by inventors Soheil Ghiasi and Daniel Fong, filed on 21 November 2016. The contents of the above-listed applications are hereby incorporated herein by reference.

BACKGROUND

Field

The disclosed embodiments generally relate to non-invasive techniques for monitoring the health of a fetus in utero. More specifically, the disclosed embodiments relate to a technique for performing robust, clinical-grade transabdominal fetal pulse oximetry.

Related Art

Physicians currently use cardiotocography (CTG) to monitor fetal well-being during active labor. This technique evaluates the temporal relationship between uterine contractions and changes in the fetal heart rate to identify signs of distress. It is thought that deceleration in the fetal heart rate after a uterine contraction is a sign of fetal distress. If occurring over a long duration, it can be an appealing option to perform an operative intervention (i.e., C-section) to quickly remove the child. However, since its introduction, CTG has been shown to have a high false-positive rate, which has partly led to a significant rise in emergency C-sections without reducing the rates of adverse fetal outcomes. C-sections are major abdominal surgeries, which increase costs and health risks to both the mother and child, such as higher rates of type 1 diabetes, chronic lung conditions, and post-operative complications. Currently, one in three children are born via C-section in the United States, which exceeds the recommended range (10-15%) put forth by the World Health Organization. In addition to a mediocre interpretation reliability amongst obstetricians, a large proportion of C-sections are performed in response to a non-reassuring CTG trace, making it clear that this high-cost (increased C-sections) and low-benefit (no change in adverse fetal outcomes) monitoring scheme needs an alternative.

Hence, what is needed is a practical technique for assessing the health of a fetus in utero without the drawbacks of existing techniques.

SUMMARY

The disclosed embodiments relate to a system that determines a fetal blood oxygenation level. (Note that the terms "blood oxygenation" and "blood oxygen saturation" refer to the same thing and are used interchangeably throughout this specification and the appended claims.) During operation, the system activates two or more light sources, having different wavelengths, which are positioned on the abdomen of a pregnant mammal to direct light into the maternal abdomen toward a fetus. Next, the system receives a set of mixed signals from a set of photodetectors, which are positioned at different locations on the maternal abdomen to receive reflected light that traverses both maternal and fetal tissue. The system also measures a maternal heart rate through an external maternal heart rate sensor, and measures a maternal respiration rate through an external maternal respiration rate sensor. Next, the system performs a filtering operation that removes signal components associated with the maternal heart rate and the maternal respiration rate from the set of mixed signals to produce a set of fetal signals. The system then combines the set of fetal signals to produce a composite fetal signal. Finally, the system determines the fetal blood oxygenation level by performing a pulse-oximetry computation based on the composite fetal signal.

In some embodiments, while combining the set of fetal signals, the system computes a dynamic weighted average of the set of fetal signals based on dynamic coefficients, which are adjusted based on evolving confidence factors associated with each individual mixed signal.

In some embodiments, the system additionally includes an external uterine contraction sensor for measuring uterine contractions. In these embodiments, performing the filtering operation involves removing contraction-induced signal artifacts associated with the uterine contractions to produce the set of fetal signals.

In some embodiments, for each mixed signal in the set of mixed signals, while performing the filtering operation the system performs a fast Fourier transform (FFT) operation on the mixed signal to compute a corresponding frequency-domain representation of the mixed signal. Next, the system uses the measured maternal respiration rate to filter out maternal respiration rate components from the frequency-domain representation of the mixed signal. The system also uses the measured maternal heart rate to filter out maternal heart rate components from the frequency-domain representation of the mixed signal. The system additionally uses the measured uterine contractions to filter out contraction-induced signal artifacts from the frequency-domain representation of the mixed signal.

In some embodiments, the two or more light sources emit light at two or more different wavelengths, including wavelengths $\lambda_1$ and $\lambda_2$, which lie on opposite sides of an isosbestic point of an absorption curve for Hb and $HbO_2$. In these embodiments, the system performs the pulse-oximetry computation on an AC component of the fetal signal associated with pulsating fetal tissue, which includes arterial blood, for each of the wavelengths $\lambda_1$ and $\lambda_2$, and a DC component of the fetal signal associated with non-pulsating fetal tissue for each of the wavelengths $\lambda_1$ and $\lambda_2$.

In some embodiments, the wavelength $\lambda_1$ substantially equals 735 nm, and the wavelength $\lambda_2$ substantially equals 850 nm.

In some embodiments, while producing the set of fetal signals, the system computes a corresponding fetal heart rate for each fetal signal in the set of fetal signals. The system also combines the corresponding fetal heart rates to produce a composite fetal heart rate, wherein the composite fetal heart rate is used while determining the fetal blood oxygenation level.

In some embodiments, the system also measures a fetal heart rate through an external fetal heart rate sensor, and then uses the measured fetal heart rate while determining the fetal blood oxygenation level.

In some embodiments, the system measures a fetal heart rate through an external fetal heart rate sensor, and measures uterine contractions through an external uterine contraction sensor. Next, the system uses a fetal heart rate tracing technique that analyzes the measured fetal heart rate and the measured uterine contractions to generate a separate indicator for oxygenation of the fetus. The system then uses the separate indicator as an additional factor while determining the fetal blood oxygenation level.

In some embodiments, while determining the fetal blood oxygenation level, the system uses a piecewise-linear representation for previously determined fetal blood oxygenation levels to compute an upper bound on change in fetal blood oxygenation level over a given time period. If a rate of change associated with a currently determined fetal blood oxygenation level exceeds the upper bound, the system caps the currently determined fetal blood oxygenation level based on the upper bound.

In some embodiments, if the set of photodetectors includes only a single photodetector, only a single mixed signal is received, which means that only a single fetal signal is produced by the filtering operation, and this single fetal signal is used as the composite fetal signal.

In some embodiments, the two or more light sources include two or more near-infrared light-emitting diodes (LEDs) that emit light at two or more wavelengths.

In some embodiments, the set of photodetectors comprise silicon photodiodes.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), application-specific instruction processors (ASIPs), and other programmable-logic devices now known or later developed. When the hardware modules are activated, the hardware modules perform the methods and processes included within the hardware modules.

Implementation Details

Transabdominal fetal pulse oximetry (TFO) can potentially improve fetal outcomes by providing physicians with a more objective metric of fetal well-being, namely fetal oxygen saturation. This technique uses light to investigate the underlying fetal tissue through a reflectance-based optical probe placed on the maternal abdomen. Variations in the diffused light intensity signal are caused by physiological changes in tissue composition, and can be analyzed to estimate the fetal oxygen saturation. A high-level diagram of transabdominal fetal pulse oximetry (TFO) can be seen in FIG. 1A.

Figure 1A:
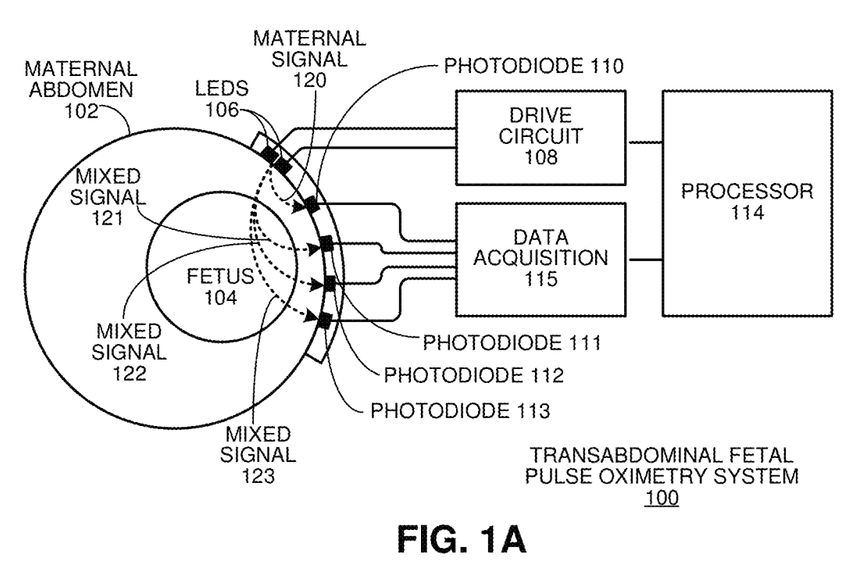
FIG. 1A illustrates a transabdominal fetal pulse oximetry system in accordance with the disclosed embodiments.

FIG. 1A illustrates a transabdominal fetal pulse oximetry system 100, which includes a light source comprising a set of two or more light-emitting diodes (LEDs) 106 that emit light at two or more wavelengths. As illustrated in FIG. 1A, LEDs 106 are positioned on a maternal abdomen 102 to direct light toward a fetus 104. Note that LEDs 106 are powered by a drive circuit 108, which operates under control of a processor 114. A photodetector comprising a photodiode 110 is positioned on the maternal abdomen 102 to receive reflected light that traverses only maternal tissue and in response produces a "maternal signal" 120. Other photodetectors comprising photodiodes 111-113 are positioned on the maternal abdomen 102 to receive reflected light that traverses both maternal and fetal tissue, and in response produces mixed signals 121-123, which include contributions from both maternal and fetal tissue. The signals 120-123 from photodiodes 110-113 feed through a data acquisition unit circuit 115 that includes a trans-amplifier and an analog-to-digital (A/D) converter, which converts analog electrical signals from photodiodes 110-113 into a sequence of digital samples. These digital samples feed into processor 114, which performs a frequency-domain and/or time-domain filtering operation to remove maternal signal components from mixed signals 121-123 to produce a corresponding set of fetal signals (not shown), and then determines the fetal blood oxygenation level by performing a pulse-oximetry computation based on the fetal signals. This process is described in more detail below.

During operation of the system illustrated in FIG. 1A, LEDs 106 shine light through maternal tissue and onto fetus 104, which is typically located several centimeters below the skin. Arterial pulsations from the maternal and fetal heartbeats cause small changes in the tissue's light absorption, and are seen as slight changes in the diffuse reflectance when measured at the surface of maternal abdomen 102. By measuring this change in the diffused light signal, oximetry calculations are performed as described below.

Figure 1B:
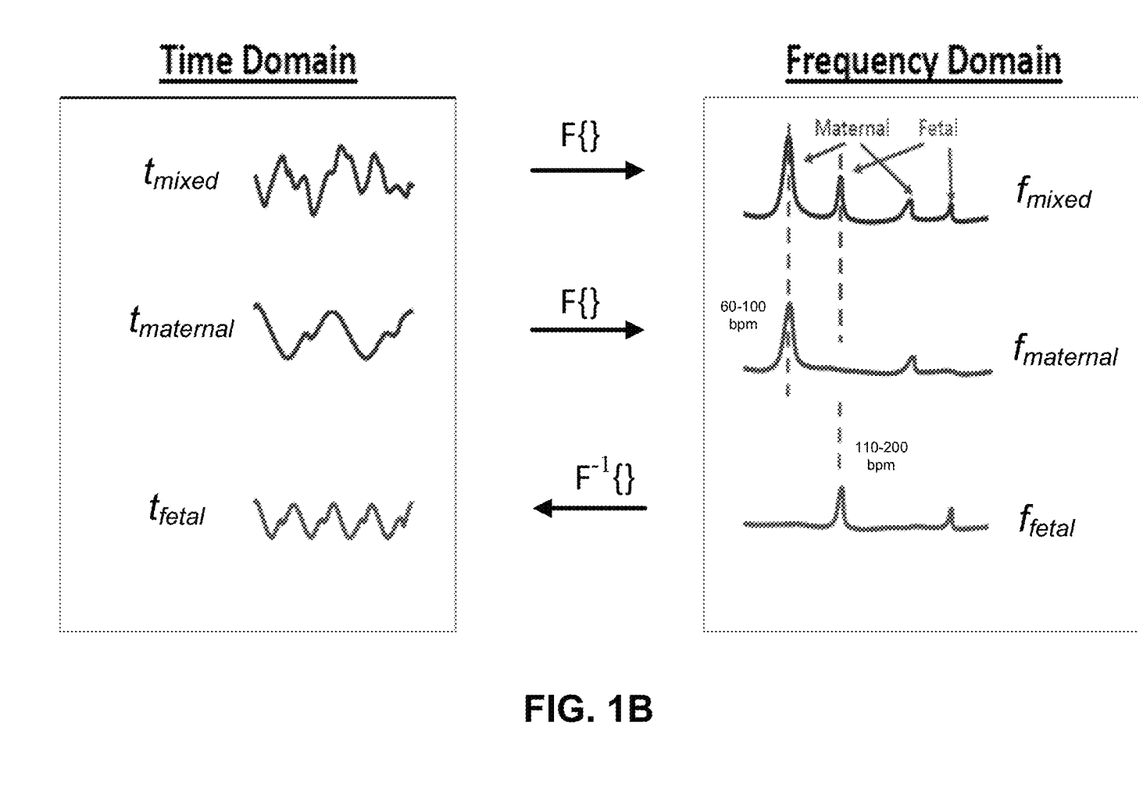
FIG. 1B illustrates how a fetal signal can be extracted using frequency-domain filtering in accordance with the disclosed embodiments.

A number of techniques to extract the weak fetal signal from the mixed signal are currently under investigation. One approach is to use adaptive-filtering techniques, which are well-suited to noise-cancellation type problems. Another approach is through frequency-domain filtering. This is illustrated in FIG. 1B, which presents a diagram illustrating time domain representations of a mixed signal ($t_{mixed}$), a maternal signal ($t_{maternal}$) and a fetal signal ($t_{fetal}$). FIG. 1B also illustrates frequency-domain representations of the mixed signal ($f_{mixed}$), the maternal signal ($f_{maternal}$) and the fetal signal ($f_{fetal}$). Because the fetal heart rate (110-200 BPM) is typically faster than the maternal heart rate (60-100 BPM), each signal's primary and secondary harmonics can be seen as peaks in the power spectral density estimation. This makes it possible to remove the maternal contribution from the mixed signal.

In general, light-based measurement modalities operate by sending a known light signal into the body, where it is modified by the human tissue, and observed some distance away. In TFO, both maternal and fetal physiology causes the tissue composition to change, resulting in a mixed (maternal+fetal) signal. Since photons must first travel through the mother's abdomen before reaching the fetus, any photons containing fetal information will be corrupted with maternal noise. In addition, the number of photons that reach the fetus is highly dependent on the fetal depth, which varies among patients and as pregnancy progresses. These structural and physiological dynamics make extracting the fetal signal challenging.

To address the fetal signal extraction problem, we propose a contextually-aware approach that extracts the fetal signal by incorporating additional information about the physical system (physiological, spatial, and temporal). It does this by using knowledge about the mother's physiology to reduce the maternal noise (physiological), incorporating spatial information from multiple detectors to increase robustness to unknown changes in fetal depth (spatial), and using historical measures of the fetal signal to improve and validate new estimates of the fetal signal (temporal). This represents a tightly-coupled cyber-physical system where the proposed contextually-aware approach incorporates knowledge of the physical system to process the raw measurements in the cyber-system, and expose an underlying physical signal (fetal signal).

To accomplish this, we perform the following operations. (1) First, we characterize the physical system by decomposing the mixed signal into its constituent parts and performing Monte Carlo simulations, to profile the relationship between the mixed signal and the physiological and spatial parameters. (2) Afterwards, we present the proposed contextually-aware fetal sensing approach, which incorporates information about the physical system, to extract the fetal signal, and describe the details of each sub-module. (3) Lastly, we evaluate the proposed approach using in vivo measurements captured on pregnant sheep/hypoxic fetal lambs, using our transabdominal fetal oximetry system.

Overview of Pulse Oximetry

Pulse oximetry is a non-invasive method to estimate the relative concentration of oxygenated hemoglobin in arterial blood. At its core, it uses the Beer-Lambert Law, which describes the changes in light intensity with respect to the concentration of chromophores in a medium and the relative distance between the light source and detector:

$$I_t(\lambda) = I_0(\lambda) * 10^{-\Sigma_i c_i(t) * \epsilon_i(\lambda) * L} \quad (1)$$

where $I_t$ is the measured light intensity at a detector at time t of wavelength $\lambda$, $I_0$ is the incident light intensity, $c_i$ and $\epsilon_i$ are the concentration and the molar extinction coefficient of the $i^{th}$ chromophore in the medium, and L is the path-length a photon takes to get to the detector from the light source. This can be written in terms of the relative change in absorption ($\Delta A$) between times t1 and t2 in the Modified Beer-Lambert Law (MBLL):

$$\Delta A = -\log_{10}(I_{t2}(\lambda)/I_{t1}(\lambda)) = \Sigma \Delta c_i * \epsilon_i * \langle L \rangle \quad (2)$$

The expected photon path-length ($\langle L \rangle$) is used here since discontinuities in the refractive index in a medium can cause photons to non-deterministically scatter from their initial trajectory.

When the medium is human tissue, cardiac contractions cause arterial vascular tissue to pulsate accordingly. This results in small, periodic dips in light-intensity seen at a detector, also known as a photoplethysmogram (PPG), and allows the optical capture of a person's heart rate. In addition, since oxy- and deoxy-hemoglobin ($HbO_2$ and $Hb$, respectively) absorb light at different levels in the red and near-infrared (NIR) spectral regions, analyzing the depth of light attenuation ($\Delta A$) from PPGs captured at these wavelengths can be used to infer the arterial blood-oxygen saturation ($SpO_2$).

$$SpO2 = C_{Hbo2}/(C_{HbO2} + C_{Hb}) \quad (3)$$

In pulse oximetry, $SpO_2$ is proportional to a modulation ratio (R) which is defined as the ratio of two PPGs taken in the red ($\lambda 1$) and NIR ($\lambda 2$) wavelengths.

$$R = \frac{\Delta A_{\lambda 1}}{\Delta A_{\lambda 2}} = \frac{\log_{10}(I_{systole,\lambda 1} / I_{diastole,\lambda 1})}{\log_{10}(I_{systole,\lambda 2} / I_{diastole,\lambda 2})} \propto SpO2 \qquad (4)$$

This proportionality factor is empirically determined using a large number of healthy volunteers through the gold-standard invasive blood-gas analysis measurements during controlled desaturation experiments.

Transabdominal Fetal Pulse Oximetry

Transabdominal fetal pulse oximetry (TFO) is a fully non-invasive technique to measure fetal oxygen saturation. This is accomplished by sending photons through the maternal abdomen to investigate the underlying fetal tissue using a reflectance-based optical probe (optode). The photons propagate through the maternal and fetal tissues, which causes the light intensity (signal) to vary according to the Beer-Lambert Law. Some of the photons that reach the fetus diffuse back toward the skin surface and are captured by a photodetector, where the resulting mixed (maternal+fetal) signal is measured, processed, and analyzed to extract the fetal signal, which is used to estimate fetal oxygen saturation through conventional pulse oximetry calculations. A high-level view of this technique is illustrated in FIG. 1A.

Mixed Signal Problem: In TFO, photons that contain fetal information must make a round-trip through the mother's abdominal wall before reaching a detector. However, physiological processes cause temporal changes in the mother's tissue composition, which alters the signal. Expanding the MBLL for both maternal and fetal tissues, the signal measured at a detector can be written as:

$$\Delta A = \frac{1}{\ln(10)} \left( \Delta \mu_{a,mat} * \langle L_{mat} \rangle + \Delta \mu_{a,fet} * \langle L_{fet} \rangle \right) + \xi \qquad (5)$$

where $\Delta A$ is the measured change in absorptivity at a detector, $\Delta \mu_{a,mat}$ and $\Delta \mu_{a,fet}$ are the changes in absorption coefficients caused by maternal and fetal tissues respectively, $\langle L_{mat} \rangle$ and $\langle L_{fet} \rangle$ are the expected partial pathlengths photons take to reach the detector through respective tissues, and $\xi$ represents other noise factors seen in the measurement (e.g., thermal noise) caused by the physical components used and is considered to be Gaussian-distributed with zero-mean. Note that we use the absorption coefficient ($\mu_a$) here instead of the molar extinction coefficient ($\epsilon$). Both provide a measure of light attenuation and are related by $\mu_a = \ln(10) * \epsilon * c$.

In order to estimate the fetal oxygenation using Equation 4, the fetal signal must be extracted from the mixed signal. Given the stochastic nature of light scattering and absorption, decoupling the maternal and fetal signals can be challenging. One approach is to use a conventional pulse oximeter on the mother's finger, to estimate the maternal contribution and remove it from the mixed signal. This helps to provide an additional measure of the mother's cardiac response, but may not fully represent the signal seen at the maternal abdomen, where respiration effects are more evident. Further measures of the mother's physiology may be helpful in fully removing the maternal contribution from the mixed signal.

Fetal Depth Variations: Prior to birth, the fetus resides in the uterus and is typically located several centimeters within the maternal abdomen. For highly-scattering materials like tissue, this is optically deep, meaning that only a small proportion of photons reaching a detector will have traversed fetal tissues. In general, signals seen at the skin surface are more sensitive to changes in the superficial (i.e., maternal) tissues, thus the maternal noise dominates the mixed signal.

For reflectance-mode sensors, the relative distance between the light source and photodetector (source-to-detector or SD distance) plays an important role in increasing the depth of tissue investigated. The larger the SD distance, the deeper the tissue being investigated but at a cost of overall light intensity (strength). Optimizing this parameter can be difficult, since patient variability can cause the fetal depth to vary drastically. This can occur among different patients, or as the fetus moves through the birth canal during natural delivery, and causes the optimal SD distance to vary among patients and over time. To design a clinically-robust TFO system, it is important that the fetal signal extraction must be robust to both inter- and intra-patient variability.

Overview of Context-Aware TFO

As previously described, the mixed signal is a result of changes in tissue composition caused by maternal and fetal physiology. In addition, the signal's sensitivity to fetal tissues is highly dependent on anatomical parameters like fetal depth. Since tissue is a highly-scattering material, small changes in fetal depth can have significant effects on the ability to capture sufficient fetal information. To address this problem, we propose a contextually-aware approach that can extract the fetal signal by using additional knowledge about the physical system, namely physiological, spatial, and temporal information. We first characterize the physical system by decomposing the mixed signal into its constituent parts, and simulate photon propagation through representative tissue models to profile the relationship between spatial parameters to the mixed signal. Next, we present the contextually-aware approach and describe its various sub-modules in detail. Lastly, we evaluate the efficacy of the approach to identify the fetal signal, by developing a TFO system prototype and capturing in vivo measurements on pregnant sheep.

Characterizing the Physical System

We characterize the physical system in order to understand its effect on the mixed signal. In particular, we decompose the mixed signal into maternal and fetal components and describe the physiological changes that cause the light intensity to vary, and simulate photon propagation through representative tissue models to profile the relationship between fetal depth, SD distance, and fetal signal sensitivity (i.e., the proportion of signal that contains fetal information).

A. Decomposing the Mixed Signal

To understand the relationship between the mixed signal and the underlying physiology it describes, we decompose the mixed signal into the maternal and fetal components and rewrite Equation 5 as:

$$\Delta A = \Delta A_{mat} + \Delta A_{fet} + \xi \qquad (6)$$

where $\Delta A_{mat}$ and $\Delta A_{fet}$ are the changes in absorptivity due to maternal and fetal tissues respectively. In TFO, identifying $\Delta A_{fet}$ is the goal. These changes are caused by the slight arterial expansion from heart contractions occurring at the fetal heart rate (FHR), typically occurring between 2-5 Hz. As described above, this signal forms the basis upon which fetal oxygen saturation can be calculated.

Physiological changes in the maternal tissue $\Delta A_{mat}$ are also present in the mixed signal. Some of these changes are caused by the mother's respiration and cardiac cycles:

$$\Delta A_{mat} = \Delta A_{mat}^{Resp.} + \Delta A_{mat}^{Cardiac} \qquad (7)$$

In the cardiac cycle, arterial vascular tissues expand slightly with each heart contraction, which increases the blood-tissue volume ratio. Depending on the tissue perfusion, the amount this rises typically varies between 2-10%. While this is a small percentage, it is enough to create a PPG waveform that is used in conventional pulse oximetry. This maternal PPG waveform is synchronous with the maternal heart rate (MHR), which typically occurs between 1-2 Hz. A number of common medical devices can be used to measure the MHR, including electrocardiogram (ECG) and conventional pulse oximeters.

Similarly, artifacts caused by respiration (breathing) may also be present in $\Delta A_{mat}$. These respiratory induced variations (RIV) are thought to be caused by changes in the peripheral venous pressure and increased rate of venous return. While the variations change synchronously with respiration rate (RR), the variation intensity is highly variable, pending ventilation and physical parameters like tidal volume, body position, and probe location. Typically, respiration occurs between 0.1-0.5 Hz. Respiratory rate can be monitored through non-invasive nasal capnography.

B. Maternal-Fetal Contribution via Monte Carlo Simulations

While physiological changes in both maternal and fetal tissues can cause the light intensity to change, their relative contribution to the mixed signal can vary depending on which tissues the photons traversed. Several key parameters that affect this are the optical and physical properties of the tissues. Importantly, the SD separation and fetal depth play a significant role in the ability to capture sufficient fetal information. To characterize this relationship, we simulated photon propagation through representative tissue models, and measured the fetal signal sensitivity, defined as the proportion of photons that traversed the fetal tissue to total photons seen at a detector.

Figure 2:
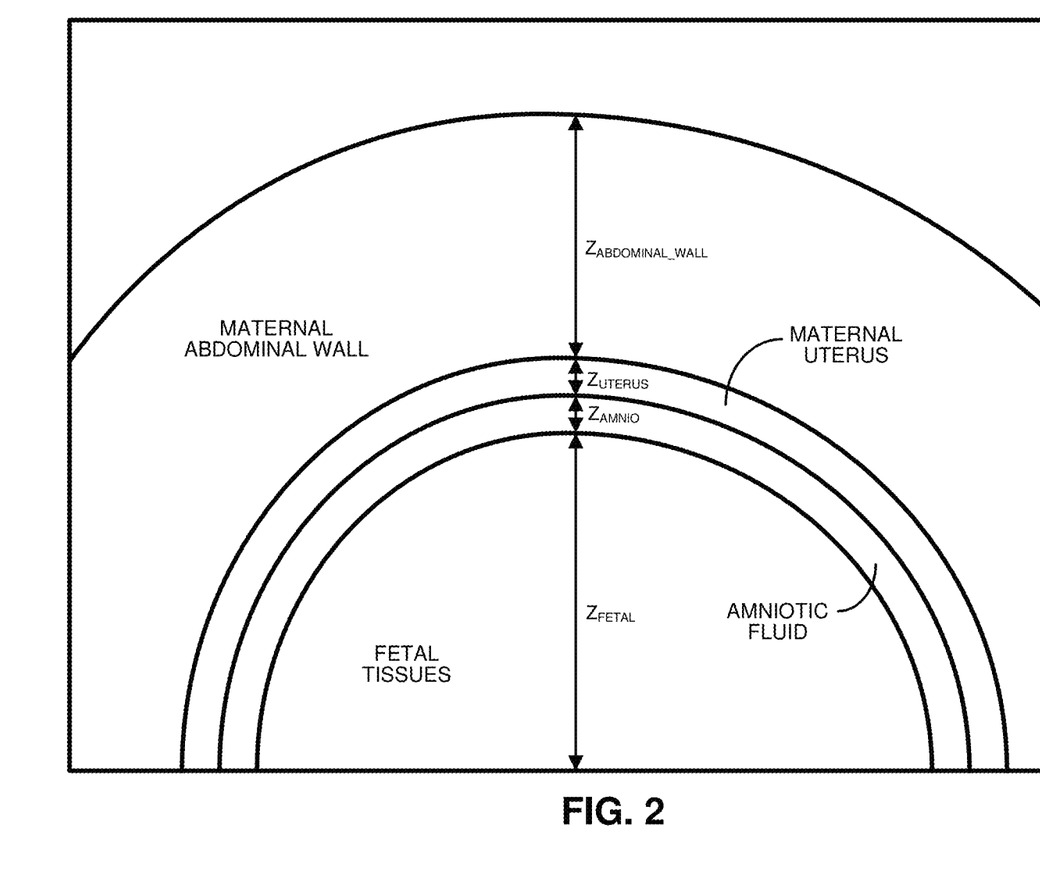
FIG. 2 illustrates a multi-layered tissue model that can be used during Monte Carlo simulations in accordance with the disclosed embodiments.
Figure 10:
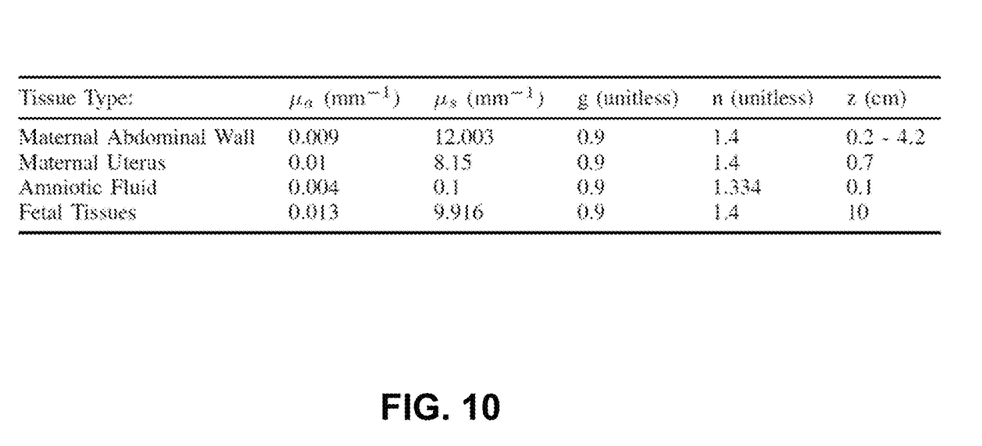
FIG. 10 presents optical properties for a tissue model in accordance with the disclosed embodiments.

Tissue Models: To model light propagation in the intrapartum environment, we developed volumetric tissue models that consisted of four spherical tissue regions, representing the maternal abdominal wall, the uterus, amniotic fluid, and the fetus, and are illustrated in FIG. 2. Their optical properties and physical dimensions were obtained through the literature, and can be seen in FIG. 10. To evaluate different fetal depths, five tissue models were developed. Each tissue model had a different abdominal wall thickness, to establish fetal depths ranging from 1 to 5 cm, matching those seen in the patient population.

Monte Carlo Simulations: Given the stochastic nature of photon propagation through highly-scattering materials like tissue, numerical techniques like Monte Carlo simulations are often used. We used a well-verified, GPU-accelerated Monte Carlo simulation to evaluate photon propagation through each of the aforementioned tissue models. In this approach, photons are injected into a tissue model, and their propagation through the tissue is monitored until they escape at the tissue surface or are extinguished by the tissue. Photon propagation through the tissue is accomplished by using the optical properties of the tissue, which describes the absorption and scattering probabilities, the scattering anisotropy, and the index of refraction. At each step, a photon is moved through the tissue and its energy is decreased according to the Beer-Lambert Law, and a probability of scattering is determined using the optical properties to seed an exponentially-weighted probability function. If a scattering event occurs, the scattering direction is obtained through the Henyey-Greenstein scattering phase function while considering Fresnel's equations at the tissue boundaries, and the photon position and direction are updated. This process is repeated until all photons are either extinguished through absorption or escape at the surface. Photons escaping at the surface that also hit a detector are recorded to analyze information about the tissues they traversed.

For each tissue model, 10 simulations were performed, where each simulated 160 million photons propagating through the tissue model at a wavelength of 850 nm. Detectors were placed on the maternal abdomen with SD distances at 1.5, 3, 4.5, 7, and 10 cm. Photons exiting the tissue that interact with these detectors were recorded, to provide context on the overall signal strength and the fetal signal sensitivity.

C. Simulation Results and Discussion

Figure 3A:
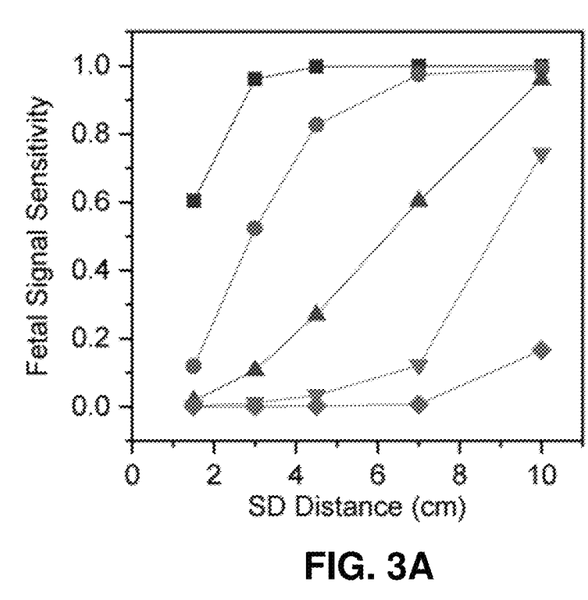
FIG. 3A presents a graph illustrating fetal signal sensitivity as a function of source-to-detector (SD) separation produced by Monte Carlo simulations in accordance with the disclosed embodiments.
Figure 3B:
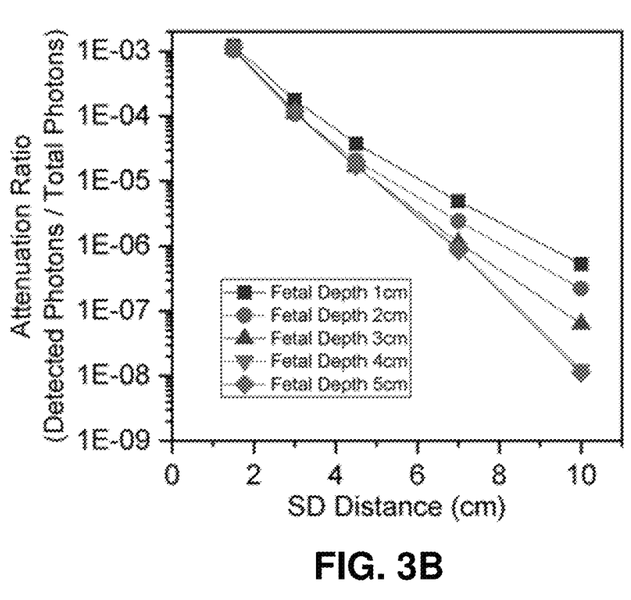
FIG. 3B presents a graph illustrating an attenuation ratio for photons as a function of SD separation produced by Monte Carlo simulations in accordance with the disclosed embodiments.

In total, 1.6 billion photons were simulated for each tissue model, which provided sufficient information for the sensitivity to converge at deeper fetal depths. Using a GPU-accelerated Monte Carlo tool, it took ~8 hrs to complete all of the simulations, which is much faster than single-threaded approaches, which would have taken several days. The effect that SD distance and fetal depth have on the fetal signal sensitivity can be seen in FIGS. 3A-3B. As we can see, detectors with large SD distances capture a higher proportion of photons that reach the fetus than those with small SD distances. In particular, the fetal signal sensitivity monotonically increases with SD distance, but decreases with fetal depth. This is expected, since it is harder for photons to reach the fetus when it is deeper. However, the attenuation ratio, defined as the number of detected photons over the total photons introduced into the skin, exponentially decreases with SD distance, as described in Equation 1. In practice, fetal depth is unavailable during the intrapartum period, thus it is difficult to determine if sufficient fetal information is being captured by a detector, without additional context.

Contextually Aware Fetal Sensing Approach

As mentioned previously, the structural and physiological dynamics of the physical system makes it difficult to decouple the fetal and maternal components from the mixed signal. We now present a contextually-aware approach that extracts the fetal signal by incorporating additional information about the physical system (physiological, spatial, and temporal). In particular, we use external measures of the mother's physiology to reduce the maternal noise (physiological), incorporate known information about the SD distance to increase robustness to unknown fetal depths through data fusion techniques (spatial), and use historical estimates to improve the ability to track and validate the fetal signal (temporal). We assume that external measures of fetal information are unavailable, as existing methods may interfere with the TFO optode due to similar placement requirements on the mother.

Figure 4:
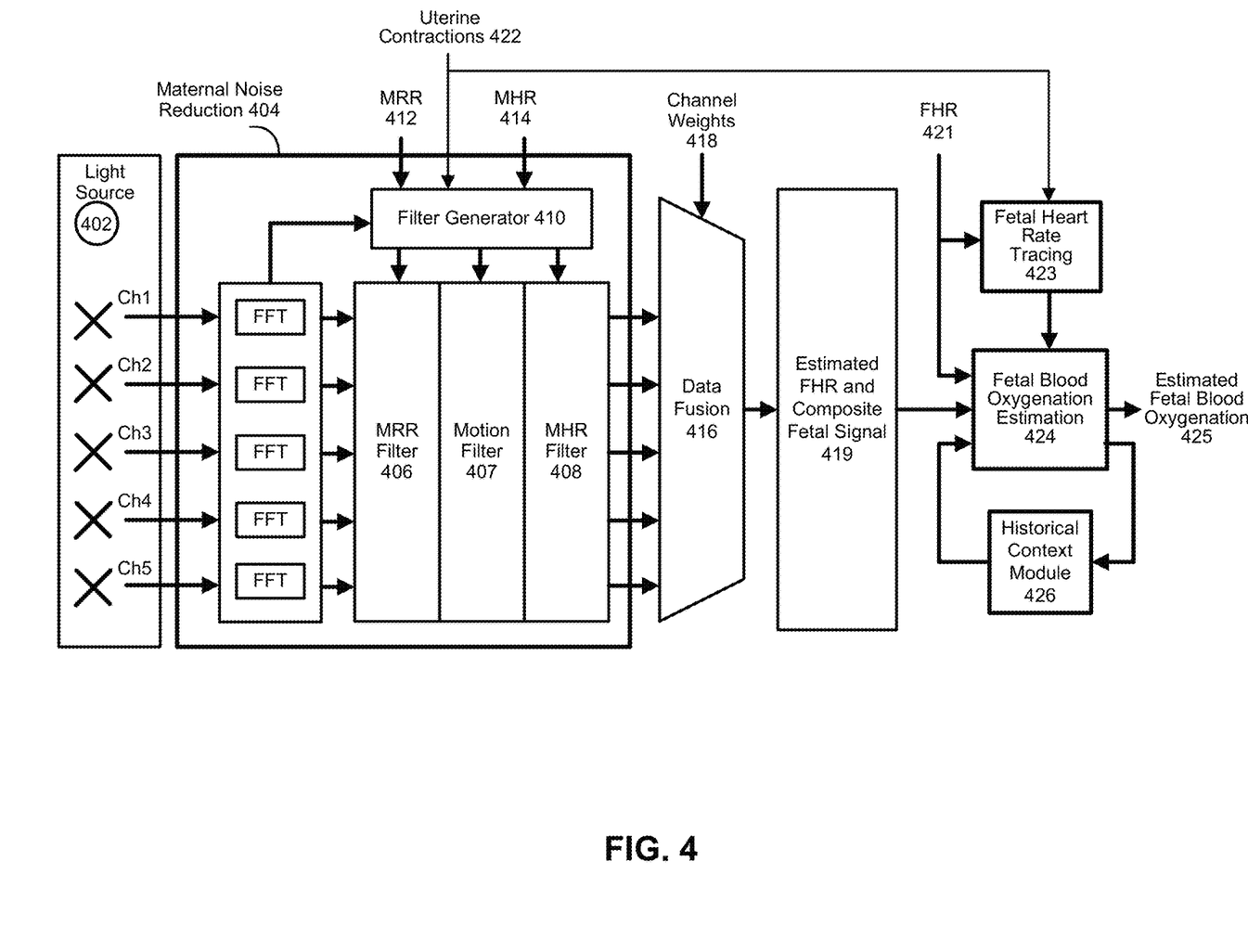
FIG. 4 presents a high-level view of a system for estimating fetal blood oxygenation levels in accordance with the disclosed embodiments.

A high-level diagram of the proposed approach is illustrated in FIG. 4. More specifically, FIG. 4 illustrates a light source 402 (such as LEDs 106 in FIG. 1A) and a number of data channels Ch1, Ch2, Ch3, Ch4 and Ch5, which carry signals received from a set of photodetectors (such as photodiodes 110-113 in FIG. 1A). These signals feed into a maternal noise reduction module 404, which performs FFT operations on the mixed signals to compute corresponding frequency-domain representations of the mixed signals. These frequency-domain representations pass through an MRR filter 406, which removes the maternal respiration component from the signal, and an MHR filter 408, which removes the maternal heart rate component from the signal. Note that MRR filter 406 and MHR filter 408 are controlled by a filter generator 410, which generates the filters based on an MRR signal 412 and an MHR signal 414, which are received from external sensors. Filter generator 410 also receives uterine contractions 422 measured by an external uterine contraction sensor, and uses the measured uterine contractions to generate a motion filter 407 that removes signal artifacts induced by the uterine contractions.

The resulting filtered signals feed through a data fusion component 416, which computes a weighted average of the filtered signals based on a set of dynamically changing channel weights 418, to produce an estimated FHR and a composite fetal signal 419. (Although it is possible to use a weighted average function to compute the estimated FHR and the composite fetal signal 419, the system is not meant to be limited to using such a weighted average. In general, other types of data fusion functions can be used.)

The estimated FHR signal 419 (along with the estimated FHR) feed into a fetal blood oxygenation estimation module 424, which analyzes the energy of the estimated FHR signal 419 at the FHR frequency to compute an estimated fetal blood oxygenation level 425 using a standard wavelength-ratio-based technique for computing blood oxygenation. Note that the system can alternatively use an FHR 421 obtained through an external FHR sensor (instead of the FHR estimated from the estimated FHR signal 419) to determine the estimated fetal blood oxygenation level 425. This alternatively generated estimate can be used as a "sanity check" for the estimate produced using the estimated FHR. As another sanity check, the system also includes a fetal heart rate tracing module 423, which uses standard fetal heart rate tracing techniques, to generate a separate indicator for the oxygenation of the fetus. This fetal heart rate tracing module 423 produces a separate indicator of the oxygenation level of the fetus (sufficiently oxygenated, indeterminate, insufficiently oxygenated) based on the FHR 421 obtained through an external FHR sensor. Fetal heart rate tracing module 423 also interprets FHR in the context of uterine contractions 422 obtained through the external uterine contraction sensor. The system can use this separate indicator as an additional factor while determining the blood oxygenation level of the fetus.

The system also includes a historical context module 426, which prevents abrupt changes in the estimated fetal blood oxygenation level that can be caused by sensor errors or other issues. Historical context module 426 uses a piecewise-linear representation for previously determined fetal blood oxygenation levels to compute an upper bound on how quickly blood oxygenation levels can change. If a rate of change associated with a currently determined fetal blood oxygenation level exceeds the upper bound, the system caps the currently determined fetal blood oxygenation level based on the upper bound. Note that the output from historic context module 426 can feed into fetal blood oxygenation estimation module 424 to provide yet another sanity check.

A. Maternal Noise Reduction

In the proposed approach, we incorporate external measures of the mother's physiology to reduce the maternal noise seen in the mixed signal. As we described previously, the source of maternal noise is respiration and cardiac contractions. Therefore, we use the mother's respiration rate (MRR) and heart rate (MHR) to generate filters that reduce their contribution to the measurements. Given the periodicity of these physiological signals, we analyze the TFO measurements in the frequency domain. First, we generate the frequency-domain representation of each channel's raw data using the fast Fourier transform and estimate their power spectral densities (PSD). The PSDs, in conjunction with external measures of the MRR and MHR, are used by the filter generator to create ideal notch filters centered at the MHR and MRR frequencies, and their associated harmonics are identified as strong peaks in the PSD at integer multiples of the fundamental frequencies. Harmonics up to 6 Hz are considered, since the fetal signal should be present within 2-5 Hz. The signals are then sent through the associated filters to reduce the maternal noise in each of the channels.

$$\Delta A_{filtered} = \Delta A_{fet} + \xi \quad (8)$$

After maternal noise reduction, the filtered signals should consist of only the fetal signal and random noise, as shown above.

B. Data Fusion

In addition to incorporating physiological information, we use data fusion to combine the measurements seen at each detector (channel) to improve the fetal signal estimation. After reducing the maternal noise, only the fetal content and random noise should remain in each of the channels. However, if the measurements are captured from a detector with a small SD separation, they may not contain sufficient fetal information (i.e., $\Delta A_{fet} \approx 0$), whereas channels with a larger SD distance will have higher fetal sensitivity but capture fewer photons overall. Importantly, the fetal sensitivity monotonically increases with SD distance. We use this information to combine the measurements from each channel using a weighted-sums approach where the weights represent the SD distance for respective detectors, thus providing a measure of relative fetal information contained in that channel.

$$\Delta A_{wsums} = \sum_i w_i * \Delta A_{filt,i} = \sum_i w_i * (\Delta A_{fet,i} + \xi_i) \quad (9)$$

As seen in FIG. 3, the shape of the fetal sensitivity to SD distance relationship changes with fetal depth. However, fetal depth is an unavailable parameter; thus, this knowledge cannot be used. For this reason, we define our weights as linear, evenly-separated weights between 0 and 1, where the weight for the largest SD distance is assigned the value of 1 and smaller SD distances are assigned values closer to 0. This linear-weighting approach aims to improve robustness to unknown changes in fetal depth.

In addition to incorporating spatially-aware sensing through this data fusion technique, another benefit is that the variance of $\xi$ is reduced in the fused signal. Since $\xi_i$ represents the random, Gaussian-distributed zero-mean random variable seen in the $i^{th}$ channel, the expectation of $\Sigma w_i * \xi_i$ will also be a Gaussian-distributed, zero-mean random variable with reduced variance, thus improving the fetal signal-to-noise ratio.

C. Fetal Signal Estimation

After data fusion, the resulting signal is then sent to the fetal signal estimation module. In a simple manner, this module uses the power spectral density of the fused signal, and searches for the maximum power within lower and upper bounds of typical fetal heart rates. We define the FHR prior as having a lower bound of 2 Hz and an upper bound of 5 Hz, as characterized in the literature. This simple approach is possible, because of the processing from earlier modules which reduced the maternal noise and incorporated spatial context into the fused signal.

D. Historical Context Module

Historical fetal blood oxygenation estimates are used to generate a prediction model (piecewise-linear representation) used to predict the next fetal blood oxygenation level ($FBO_{pred}$), and determine the validity of the estimated fetal blood oxygenation level ($FBO_{est}$). If the estimate is similar to the prediction, then $FBO_{est}$ is deemed valid and is passed through to the output. However, if they differ drastically, we consider the estimate to be invalid, and use $FBO_{pred}$ as the result.

The resulting fetal blood oxygenation is then stored in a historical buffer, which uses the last 30 sec of estimates to generate the next prediction model. In the case where the estimate is invalid for an extended period of time (i.e., 30 sec), we maintain the last FBO value rather than using $FBO_{pred}$.

Process of Determining a Fetal Blood Oxygenation Level

Figure 5:
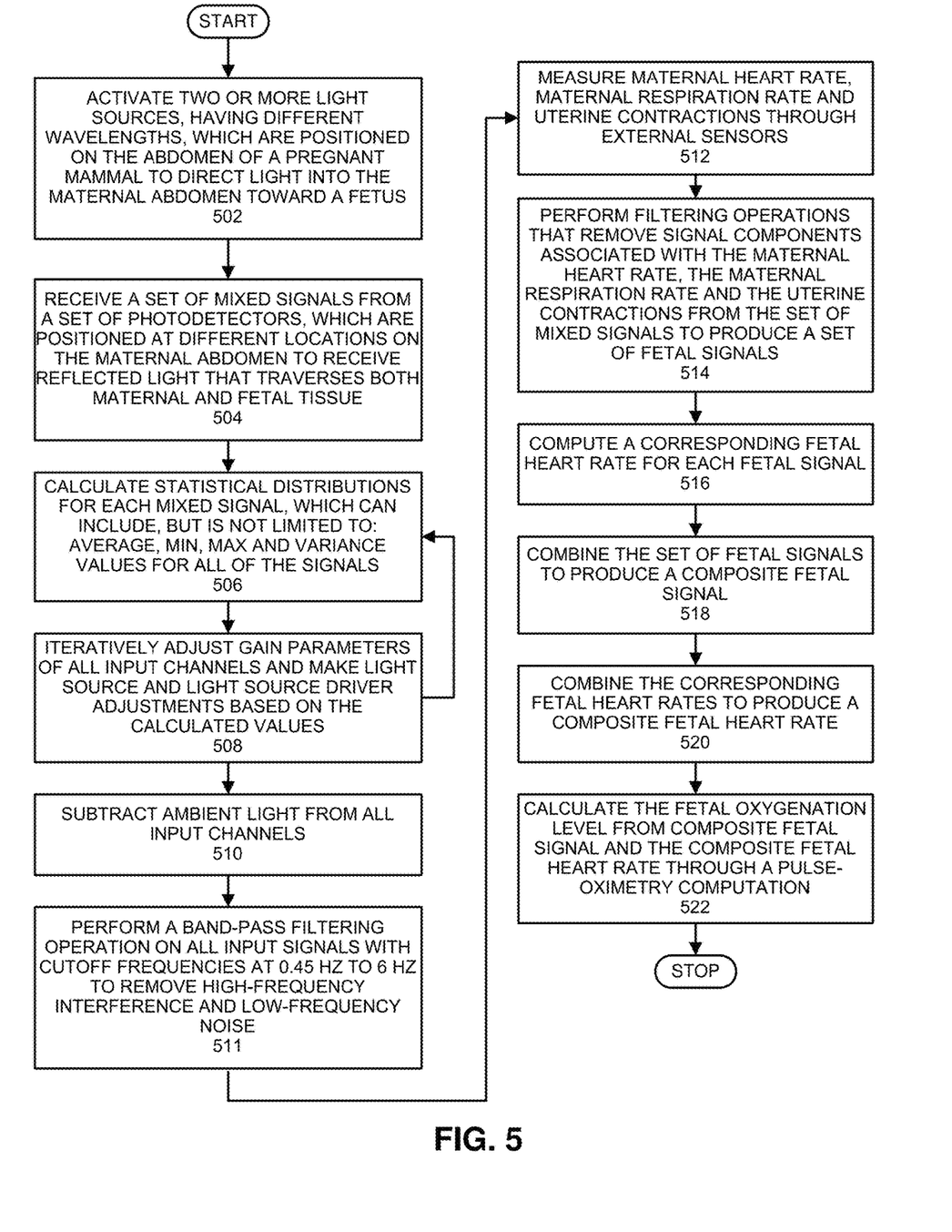
FIG. 5 presents a flow chart illustrating a process for determining a fetal blood oxygenation level in accordance with the disclosed embodiments.

FIG. 5 presents a flow chart illustrating a process for determining a fetal blood oxygenation level in accordance with the disclosed embodiments. During operation, the system activates two or more light sources, having different wavelengths, which are positioned on the abdomen of a pregnant mammal to direct light into the maternal abdomen toward a fetus (step 502). Next, the system receives a set of mixed signals from a set of photodetectors, which are positioned at different locations on the maternal abdomen to receive reflected light that traverses both maternal and fetal tissue (step 504). The system then calculates statistical distributions for each mixed signal, which can include, but are not limited to: average, minimum, maximum and variance values for all of the signals (step 506). Next, the system iteratively adjusts gain parameters of all input channels and makes light source and light source driver adjustments based on the calculated value to use the full dynamic range of the data acquisition electronics (step 508). (Note that this iterative process may involve returning to step 506 if necessary.) Next, the system subtracts ambient light from all of the input channels (step 510). Note that the ambient light can be subtracted so that the resulting signals only account for light received for the emitters at the appropriate wavelengths of light associated with the emitters. The system then performs a band-pass filtering operation on all input signals with cutoff frequencies at 0.45 Hz to 6 Hz to remove high-frequency interference and low-frequency noise (step 511). Note that such noise can be generated by power lines and low-frequency biosignals, such as signals associated with respiration and Mayer waves.

Next, the system measures maternal heart rate, maternal respiration rate and uterine contractions through external sensors (step 512). The system then performs filtering operations that remove signal components associated with the maternal heart rate, the maternal respiration rate and the uterine contractions from the set of mixed signals to produce a set of fetal signals (step 514). The system also computes a corresponding fetal heart rate for each fetal signal (step 516). The system then combines the set of fetal signals to produce a composite fetal signal (step 518), and also combines the corresponding fetal heart rates to produce a composite fetal heart rate (step 520). Finally, the system calculates the fetal blood oxygenation based on the composite fetal signal and the composite fetal heart rate through a pulse-oximetry computation (step 522).

Figure 6:
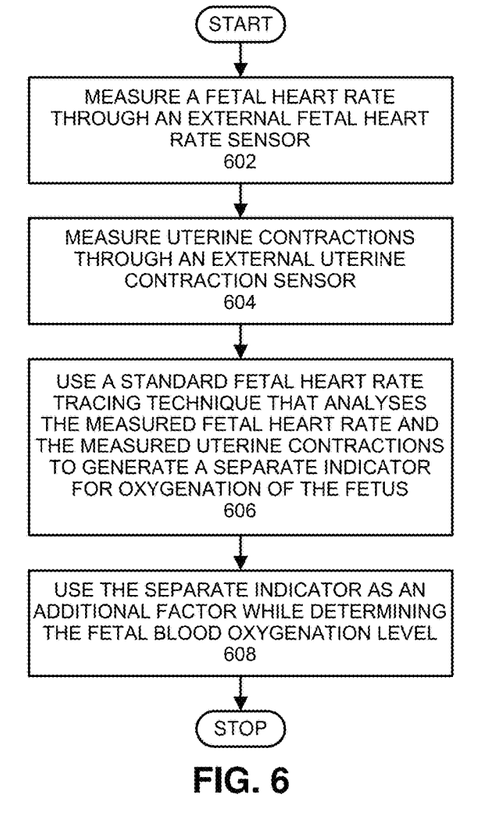
FIG. 6 presents a flow chart illustrating a process for generating a separate indicator for oxygenation for the fetus in accordance with the disclosed embodiments.

FIG. 6 presents a flow chart illustrating a process for generating a separate indicator for oxygenation for the fetus in accordance with the disclosed embodiments. During this process, the system measures a fetal heart rate through an external fetal heart rate sensor (step 602), and also measures uterine contractions through an external uterine contraction sensor (step 604). The system then uses a standard fetal heart rate tracing technique that analyzes the measured fetal heart rate and the measured uterine contractions to generate a separate indicator for oxygenation of the fetus (step 606).

Next, the system uses the separate indicator as an additional factor while determining the fetal blood oxygenation level (step 608).

Figure 7:
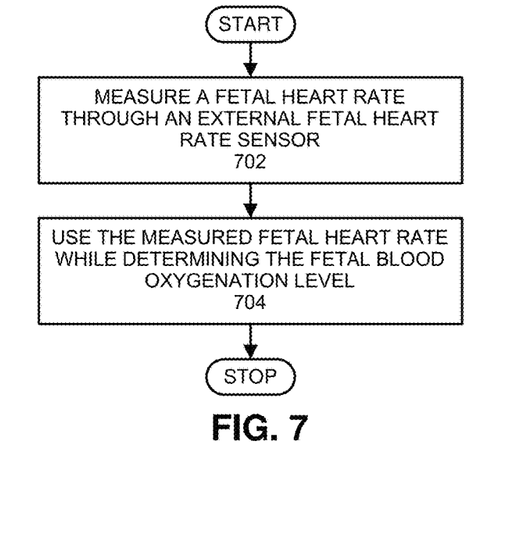
FIG. 7 presents a flow chart illustrating a process for using a directly measured fetal heart rate to facilitate determining the fetal blood oxygenation level in accordance with the disclosed embodiments.

FIG. 7 presents a flow chart illustrating a process for using a measured fetal heart rate to facilitate determining the fetal blood oxygenation level in accordance with the disclosed embodiments. During this process, the system measures a fetal heart rate through an external fetal heart rate sensor (step 702), and then uses the measured fetal heart rate while determining the fetal blood oxygenation level (step 704).

Figure 8:
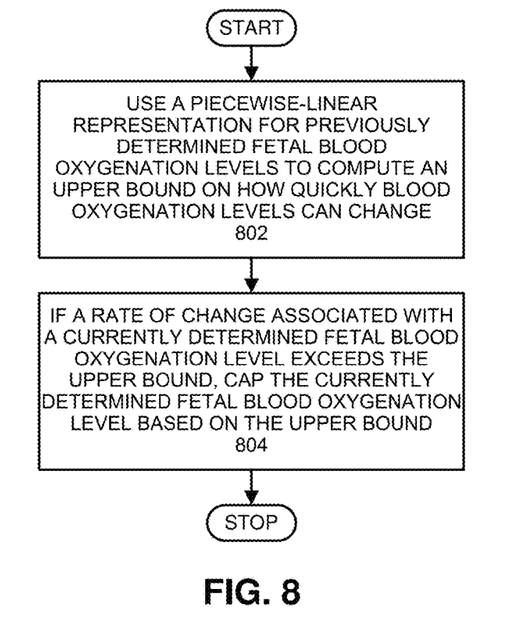
FIG. 8 presents a flow chart illustrating a process for capping a rate of change for the fetal blood oxygenation level in accordance with the disclosed embodiments.

FIG. 8 presents a flow chart illustrating a process for capping a rate of change for the fetal blood oxygenation level in accordance with the disclosed embodiments. During this process, the system uses a piecewise-linear representation for previously determined fetal blood oxygenation levels to compute an upper bound on how quickly blood oxygenation levels can change (step 802). If a rate of change associated with a currently determined fetal blood oxygenation level exceeds the upper bound, the system caps the currently determined fetal blood oxygenation level based on the upper bound (step 804).

Figure 9:
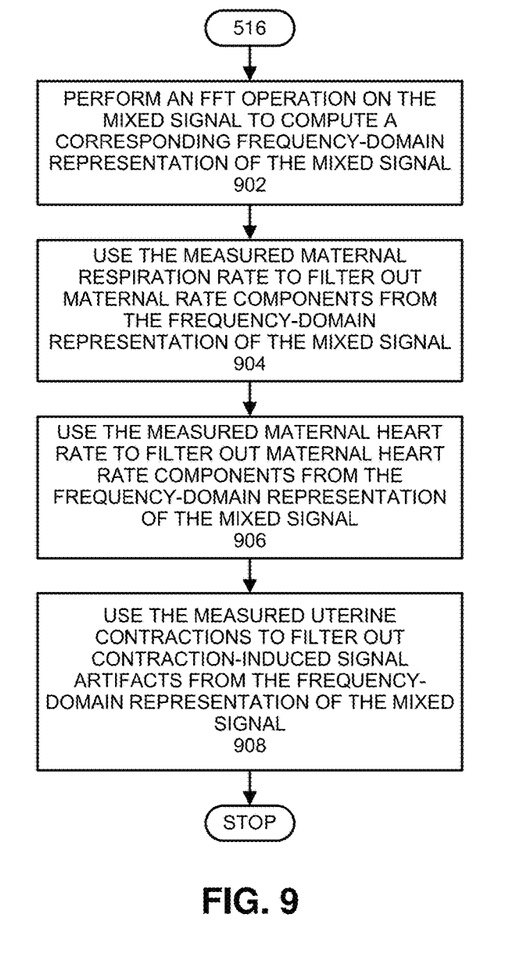
FIG. 9 presents a flow chart illustrating a process for performing a filtering operation on the set of mixed signals in accordance with the disclosed embodiments.

FIG. 9 presents a flow chart illustrating a process for performing a filtering operation on the set of mixed signals in accordance with the disclosed embodiments. (This flow chart illustrates in more detail the operations performed in step 516 of the flow chart in FIG. 5.) While performing the filtering operation for each mixed signal, the system first performs an FFT operation on the mixed signal to compute a corresponding frequency-domain representation of the mixed signal (step 902). Next, the system uses the measured maternal respiration rate to filter out maternal rate components from the frequency-domain representation of the mixed signal (step 904). The system also uses the measured maternal heart rate to filter out maternal heart rate components from the frequency-domain representation of the mixed signal (step 906). The system additionally uses the measured uterine contractions to filter out contraction-induced signal artifacts from the frequency-domain representation of the mixed signal (step 908).

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for determining a fetal blood oxygenation level, comprising:
   activating two or more light sources, having different wavelengths, which are positioned on the maternal abdomen of a pregnant mammal to direct light into a maternal abdomen toward a fetus;
   receiving a set of mixed signals from a set of photodetectors, which are positioned at different locations on the maternal abdomen to receive reflected light from the two or more light sources that traverses both maternal and fetal tissue;

measuring a maternal heart rate through an external maternal heart rate sensor;

measuring a maternal respiration rate through an external maternal respiration rate sensor;

performing a filtering operation that removes signal components associated with the maternal heart rate and the maternal respiration rate from the set of mixed signals to produce a set of fetal signals;

combining the set of fetal signals to produce a composite fetal signal by computing a dynamic weighted average of the set of fetal signals based on dynamic coefficients, which are adjusted based on evolving confidence factors associated with each individual mixed signal; and determining the fetal blood oxygenation level by performing a pulse-oximetry computation based on the composite fetal signal.

2. The method of claim 1, wherein the method further comprises measuring uterine contractions through an external uterine contraction sensor; and wherein performing the filtering operation involves removing contraction-induced signal artifacts associated with the uterine contractions to produce the set of fetal signals.

3. The method of claim 2, wherein for each mixed signal in the set of mixed signals, performing the filtering operation comprises:

performing a fast Fourier transform (FFT) operation on the mixed signal to compute a corresponding frequency-domain representation of the mixed signal;

using the measured maternal respiration rate to filter out maternal respiration rate components from the frequency-domain representation of the mixed signal;

using the measured maternal heart rate to filter out maternal heart rate components from the frequency-domain representation of the mixed signal; and using the measured uterine contractions to filter out contraction-induced signal artifacts from the frequency-domain representation of the mixed signal.

4. The method of claim 1, wherein the two or more light sources emit light at two or more different wavelengths, including wavelengths $\lambda_1$ and $\lambda_2$, which lie on opposite sides of an isosbestic point of an absorption curve for Hb and $HbO_2$; and wherein the pulse-oximetry computation is performed on an AC component of the fetal signal associated with pulsating fetal tissue, which includes arterial blood, for each of the wavelengths $\lambda_1$ and $\lambda_2$, and a DC component of the fetal signal associated with non-pulsating fetal tissue for each of the wavelengths $\lambda_1$ and $\lambda_2$.

5. The method of claim 2, wherein the wavelength $\lambda_1$ substantially equals 735 nm; and wherein the wavelength $\lambda_2$ substantially equals 850 nm.

6. The method of claim 1, wherein producing the set of fetal signals involves computing a corresponding fetal heart rate for each fetal signal in the set of fetal signals;

wherein combining the set of fetal signals to produce the composite fetal signal involves combining the corresponding fetal heart rates to produce a composite fetal heart rate; and wherein the composite fetal heart rate is used while determining the fetal blood oxygenation level.

7. The method of claim 1, wherein the method further comprises:

measuring a fetal heart rate through an external fetal heart rate sensor; and using the measured fetal heart rate while determining the fetal blood oxygenation level.

8. The method of claim 1, wherein the method further comprises:

measuring a fetal heart rate through an external fetal heart rate sensor;

measuring uterine contractions through an external uterine contraction sensor;

using a fetal heart rate tracing technique that analyzes the measured fetal heart rate and the measured uterine contractions to generate a separate indicator for oxygenation of the fetus; and using the separate indicator as an additional factor while determining the fetal blood oxygenation level.

9. The method of claim 1, wherein determining the fetal blood oxygenation level additionally comprises:

using a piecewise-linear representation for previously determined fetal blood oxygenation levels to compute an upper bound on change in fetal blood oxygenation level over a given time period; and if a rate of change associated with a currently determined fetal blood oxygenation level exceeds the upper bound, capping the currently determined fetal blood oxygenation level based on the upper bound.

10. The method of claim 1, wherein if the set of photodetectors includes only a single photodetector, only a single mixed signal is received, which means that only a single fetal signal is produced by the filtering operation, and this single fetal signal is used as the composite fetal signal.

11. The method of claim 1, wherein the two or more light sources include two or more near-infrared light-emitting diodes (LEDs) that emit light at two or more wavelengths.

12. The method of claim 1, wherein the set of photodetectors comprise silicon photodiodes.

13. A system that determines a fetal blood oxygenation level, comprising:

two or more light sources, having different wavelengths, to be positioned on a maternal abdomen of a pregnant mammal to direct light into a maternal abdomen toward a fetus;

a controller to selectively activate the two or more light sources;

a set of photodetectors, wherein each photodetector in the set of photodetectors is positioned at a different location on the maternal abdomen to receive reflected light from the two or more light sources that traverses both maternal and fetal tissue to produce a mixed signal;

a maternal heart rate sensor that measures a maternal heart rate;

a maternal respiration rate sensor that measures a maternal respiration rate; and a processing mechanism that:

receives the set of mixed signals, performs a filtering operation that removes signal components associated with the maternal heart rate and the maternal respiration rate from the set of mixed signals to produce a set of fetal signals, combines the set of fetal signals to produce a composite fetal signal by computing a dynamic weighted average of the set of fetal signals based on dynamic coefficients, which are adjusted based on evolving confidence factors associated with each individual mixed signal, and determines the fetal blood oxygenation level by performing a pulse-oximetry computation based on the composite fetal signal.

14. The system of claim 13,
wherein the system additionally includes an external uterine contraction sensor for measuring uterine contractions; and
wherein while performing the filtering operation, the processing mechanism removes contraction-induced signal artifacts associated with the uterine contractions to produce the set of fetal signals.

15. The system of claim 14, wherein for each mixed signal in the set of mixed signals, while performing the filtering operation, the computing mechanism:
performs a fast Fourier transform (FFT) operation on the mixed signal to compute a corresponding frequency-domain representation of the mixed signal;
uses the measured maternal respiration rate to filter out maternal respiration rate components from the frequency-domain representation of the mixed signal;
uses the measured maternal heart rate to filter out maternal heart rate components from the frequency-domain representation of the mixed signal; and
uses the measured uterine contractions to filter out contraction-induced signal artifacts from the frequency-domain representation of the mixed signal.

16. The system of claim 13,
wherein the two or more light sources emit light at two or more different wavelengths, including wavelengths $\lambda_1$ and $\lambda_2$, which lie on opposite sides of an isosbestic point of an absorption curve for Hb and $HbO_2$; and
wherein the pulse oximetry computation is performed on an AC component of the fetal signal associated with pulsating fetal tissue, which includes arterial blood, for each of the wavelengths $\lambda_1$ and $\lambda_2$, and a DC component of the fetal signal associated with non-pulsating fetal tissue for each of the wavelengths $\lambda_1$ and $\lambda_2$.

17. The system of claim 16,
wherein the wavelength $\lambda_1$ substantially equals 735 nm; and
wherein the wavelength $\lambda_2$ substantially equals 850 nm.

18. The system of claim 13,
wherein while producing the set of fetal signals, the computing mechanism computes a corresponding fetal heart rate for each fetal signal in the set of fetal signals;
wherein while combining the set of fetal signals to produce the composite fetal signal, the computing mechanism combines the corresponding fetal heart rates to produce a composite fetal heart rate; and
wherein the computing mechanism uses the composite fetal heart rate while determining the fetal blood oxygenation level.

19. The system of claim 13,
wherein the system further comprises a fetal heart rate sensor that measures a fetal heart rate; and
wherein the computing mechanism uses the measured fetal heart rate while determining the fetal blood oxygenation level.

20. The system of claim 13,
wherein the system further comprises a fetal heart rate sensor that measures a fetal heart rate;
wherein the system further comprises a uterine contraction sensor that measures uterine contractions;
wherein the computing mechanism uses a fetal heart rate tracing technique that analyzes the measured fetal heart rate and the measured uterine contractions to generate a separate indicator for oxygenation of the fetus; and
wherein the computing mechanism uses the separate indicator as an additional factor while determining the fetal blood oxygenation level.

21. The system of claim 13, wherein while determining the fetal blood oxygenation level, the computing mechanism additionally:
uses a piecewise-linear representation for previously determined fetal blood oxygenation levels to compute an upper bound on change in fetal blood oxygenation level over a given time period; and
if a rate of change associated with a currently determined fetal blood oxygenation level exceeds the upper bound, caps the currently determined fetal blood oxygenation level based on the upper bound.

22. The system of claim 13, wherein if the set of photodetectors includes only a single photodetector, only a single mixed signal is received, which means that only a single fetal signal is produced by the filtering operation, and this single fetal signal is used as the composite fetal signal.

23. The system of claim 13, wherein the two or more light sources include two or more near-infrared light-emitting diodes (LEDs) that emit light at two or more wavelengths.

24. The system of claim 13, wherein the set of photodetectors comprise silicon photodiodes.

* * * * *